(12) United States Patent
Griffin

(10) Patent No.: US 10,743,756 B2
(45) Date of Patent: Aug. 18, 2020

(54) MULTI-SPECTRUM RING ILLUMINATED SURGICAL CAMERA

(71) Applicant: InnovaQuartz LLC, Phoenix, AZ (US)

(72) Inventor: Stephen E. Griffin, Peoria, AZ (US)

(73) Assignee: INNOVAQUARTZ LLC, Phoenix, AZ (US)

( * ) Notice: Subject to any disclaimer, the term of this patent is extended or adjusted under 35 U.S.C. 154(b) by 0 days.

(21) Appl. No.: 16/557,074

(22) Filed: Aug. 30, 2019

(65) Prior Publication Data

US 2020/0113424 A1  Apr. 16, 2020

Related U.S. Application Data

(62) Division of application No. 16/157,478, filed on Oct. 11, 2018, now abandoned.

(51) Int. Cl.
| | | |
|---|---|---|
| A61B 1/06 | (2006.01) | |
| G02B 23/24 | (2006.01) | |
| G02B 19/00 | (2006.01) | |
| A61B 1/00 | (2006.01) | |
| A61B 1/05 | (2006.01) | |
| A61B 1/307 | (2006.01) | |
| A61B 1/018 | (2006.01) | |
| A61B 90/00 | (2016.01) | |
| H04N 5/225 | (2006.01) | |

(52) U.S. Cl.
CPC ........ *A61B 1/0676* (2013.01); *A61B 1/00096* (2013.01); *A61B 1/05* (2013.01); *A61B 1/0638* (2013.01); *A61B 1/0684* (2013.01); *G02B 19/0066* (2013.01); *G02B 23/2461* (2013.01); *A61B 1/018* (2013.01); *A61B 1/307* (2013.01); *A61B 90/361* (2016.02); *H04N 5/2254* (2013.01)

(58) Field of Classification Search
CPC ..... A61B 1/00096; A61B 1/05; A61B 1/0638; A61B 1/0676; A61B 1/0684; G02B 19/0066; G02B 23/2461
See application file for complete search history.

(56) References Cited

U.S. PATENT DOCUMENTS

| | | |
|---|---|---|
| 6,404,984 B1 | 6/2002 | Parvulescu et al. |
| 6,449,006 B1 | 9/2002 | Shipp |
| 6,551,240 B2 | 4/2003 | Henzler |
| 6,659,940 B2 | 12/2003 | Adler |
| 7,668,450 B2 | 2/2010 | Todd et al. |
| 8,202,214 B2 | 6/2012 | Doguchi et al. |
| 8,308,637 B2 | 11/2012 | Ishigami et al. |
| 8,512,232 B2 | 8/2013 | Rothberg et al. |
| 8,801,255 B2 | 8/2014 | Kudo |
| 9,826,892 B2 | 11/2017 | Dresher et al. |

(Continued)

OTHER PUBLICATIONS

Hemphill, B., Light emitting diodes and a monochrome camera to measure chemical optode response, Jan. 2013, Case Western Reserve University, Cleveland, Ohio.

(Continued)

*Primary Examiner* — Aaron B Fairchild
(74) *Attorney, Agent, or Firm* — Quarles & Brady LLP; Yakov Sidorin

(57) ABSTRACT

Multi-spectrum ring illuminated surgical cameras and scopes having a ring lens and a plurality of LEDs. The LEDs set behind an electronic imaging sensor (camera) and positioned radially about the longitudinal axis of the lens and/or scope.

12 Claims, 11 Drawing Sheets

(56) References Cited

U.S. PATENT DOCUMENTS

| | | |
|---|---|---|
| 9,838,576 B2 | 12/2017 | Haraguchi et al. |
| 2003/0050534 A1 | 3/2003 | Kazakevich |
| 2004/0062056 A1* | 4/2004 | Heine ................... A61B 5/0059 362/555 |
| 2005/0177027 A1 | 8/2005 | Hirata |
| 2005/0234296 A1 | 10/2005 | Saadat et al. |
| 2006/0173242 A1 | 8/2006 | Navok et al. |
| 2007/0038030 A1 | 2/2007 | Kaneko et al. |
| 2007/0039077 A1 | 2/2007 | Takami |
| 2008/0208006 A1 | 8/2008 | Farr |
| 2008/0283770 A1 | 11/2008 | Takahashi |
| 2009/0306474 A1 | 12/2009 | Wilson |
| 2013/0131447 A1 | 5/2013 | Benning et al. |
| 2016/0058383 A1 | 3/2016 | Hellstrom et al. |
| 2017/0353656 A1 | 12/2017 | Ramones et al. |

OTHER PUBLICATIONS

Keyence, Multi-Spectrum Vision System, 2017.

\* cited by examiner

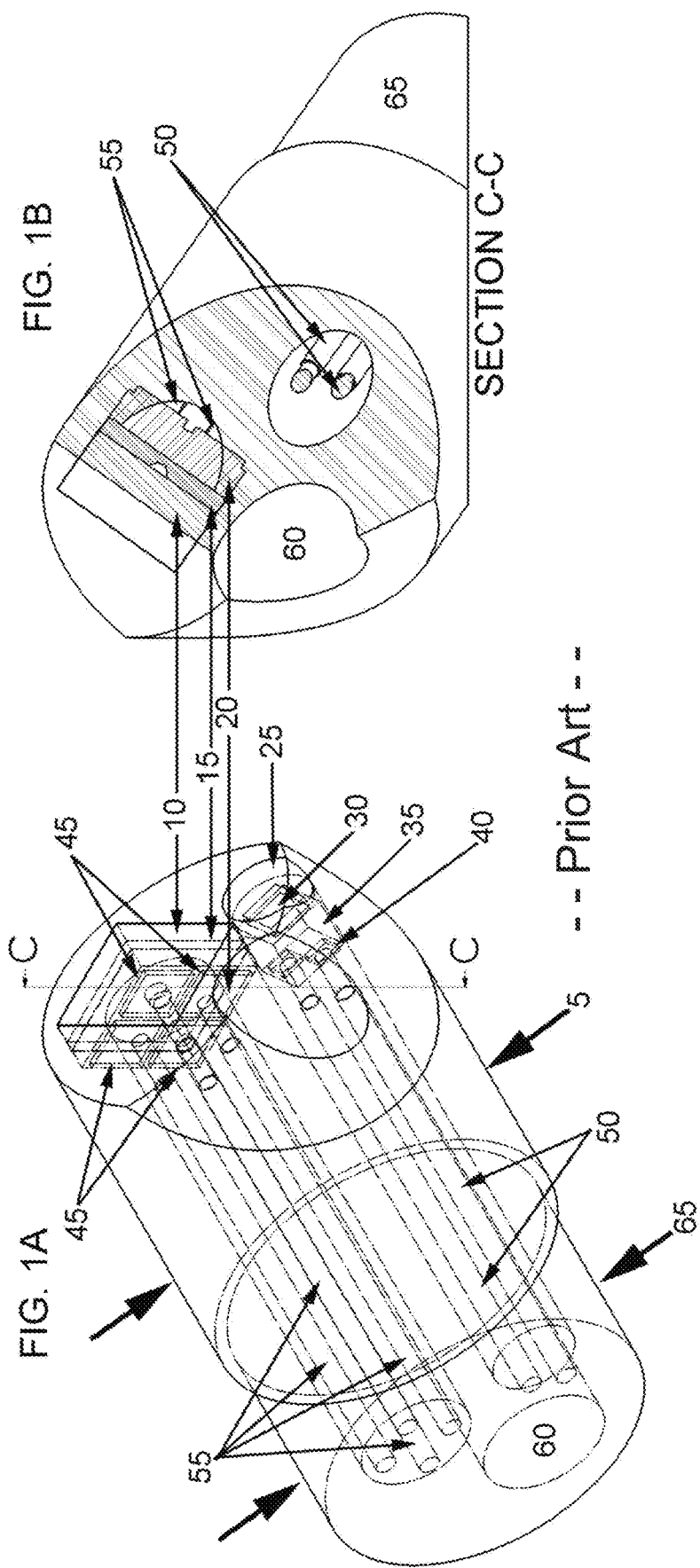

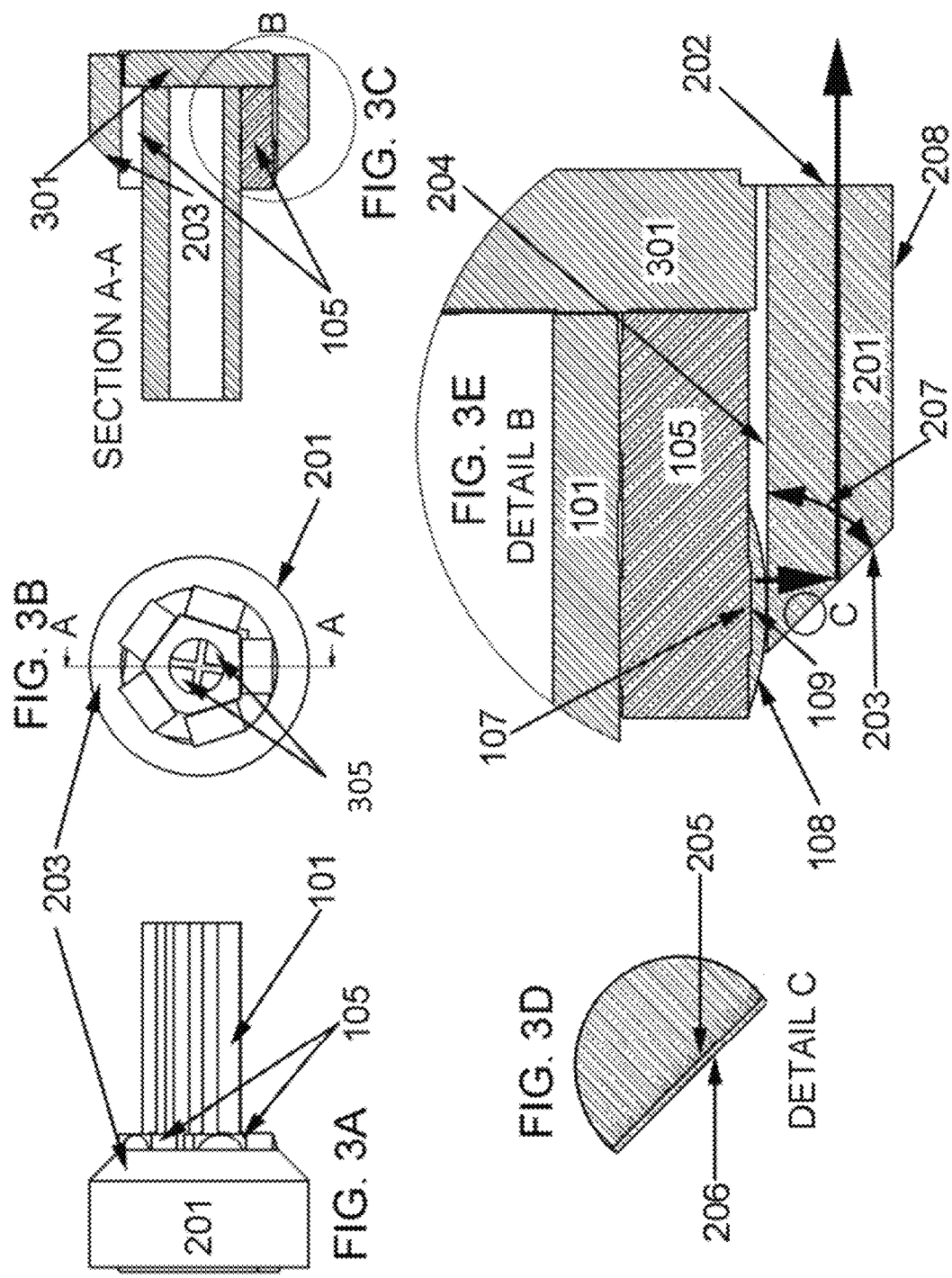

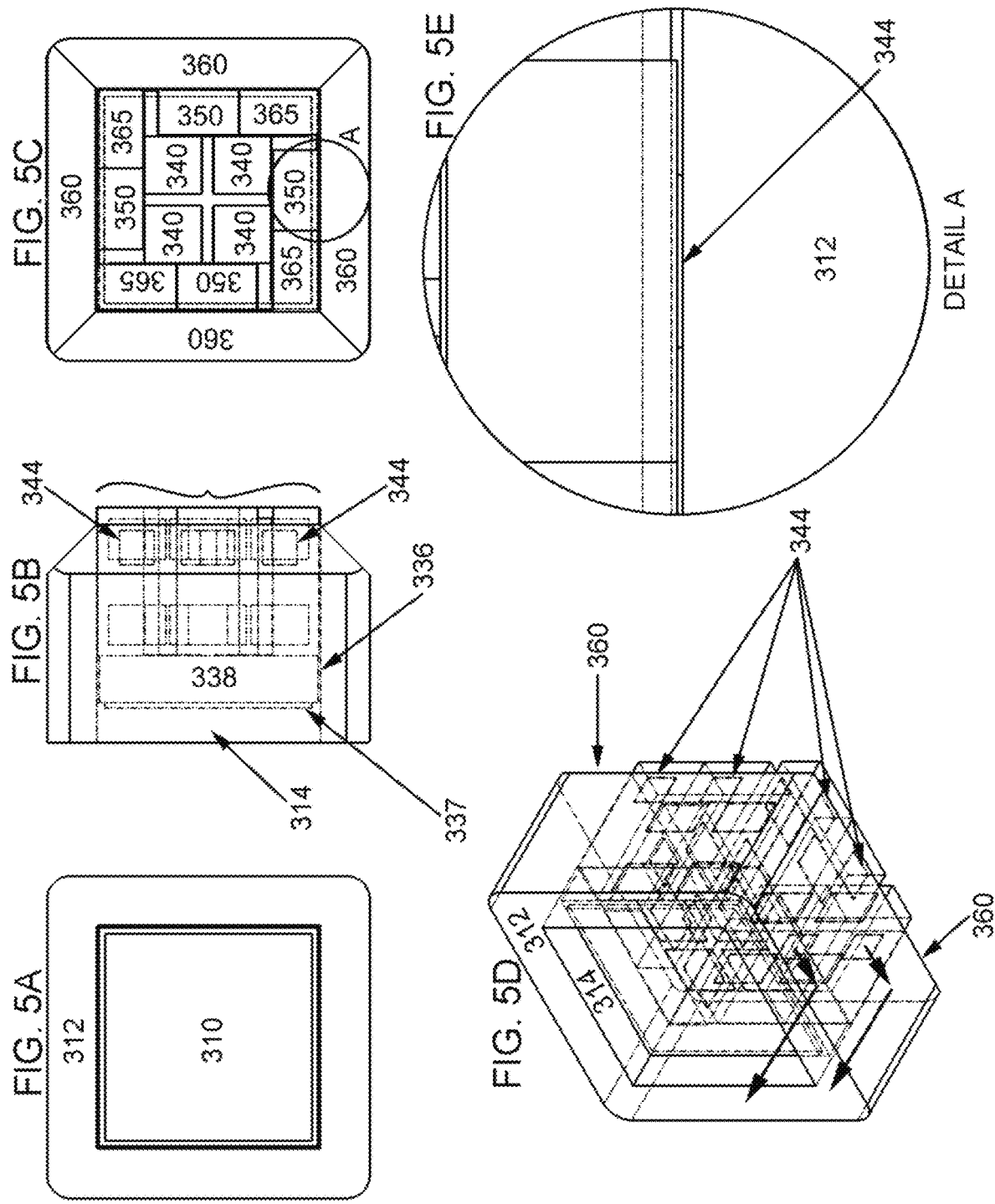

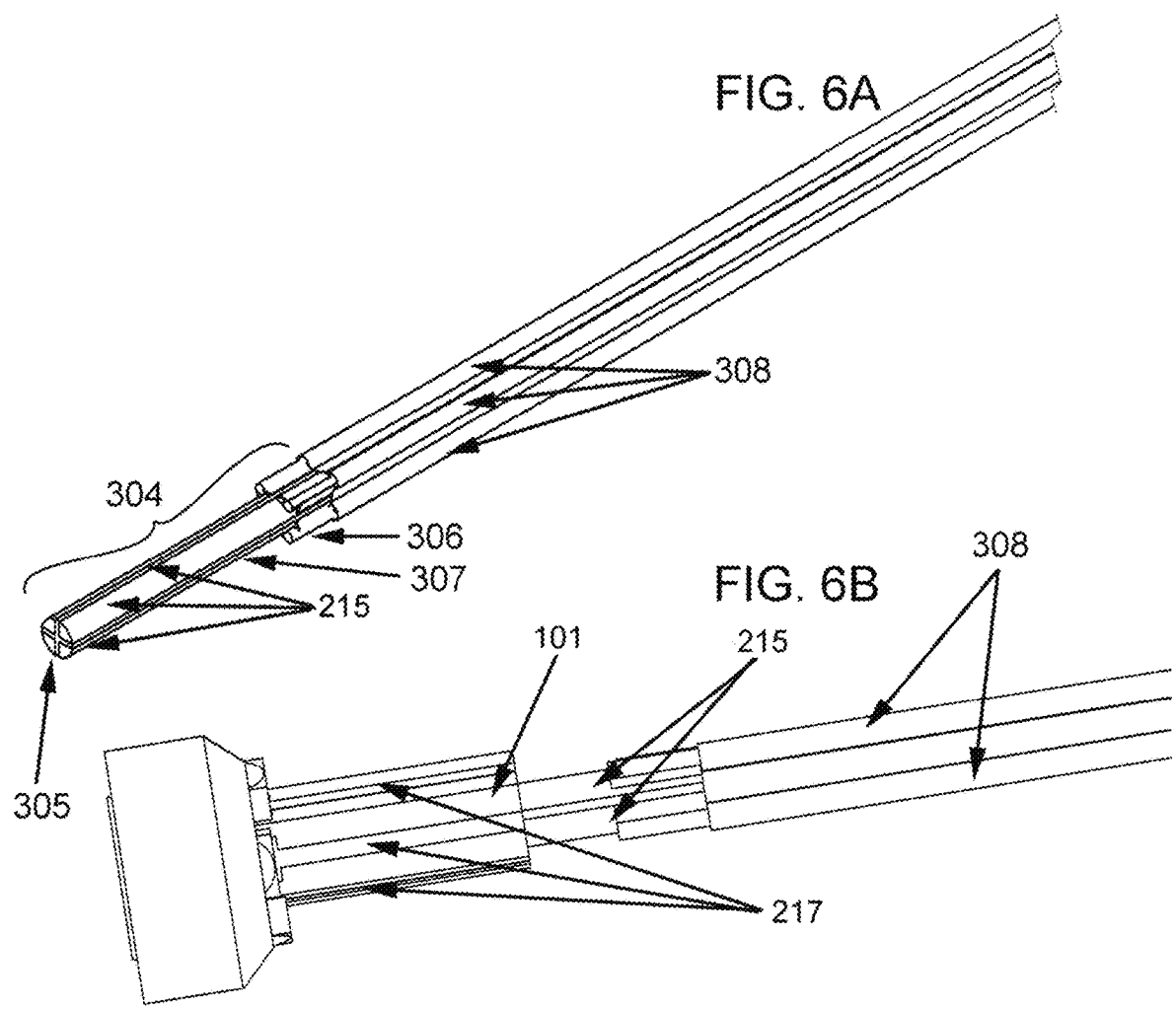

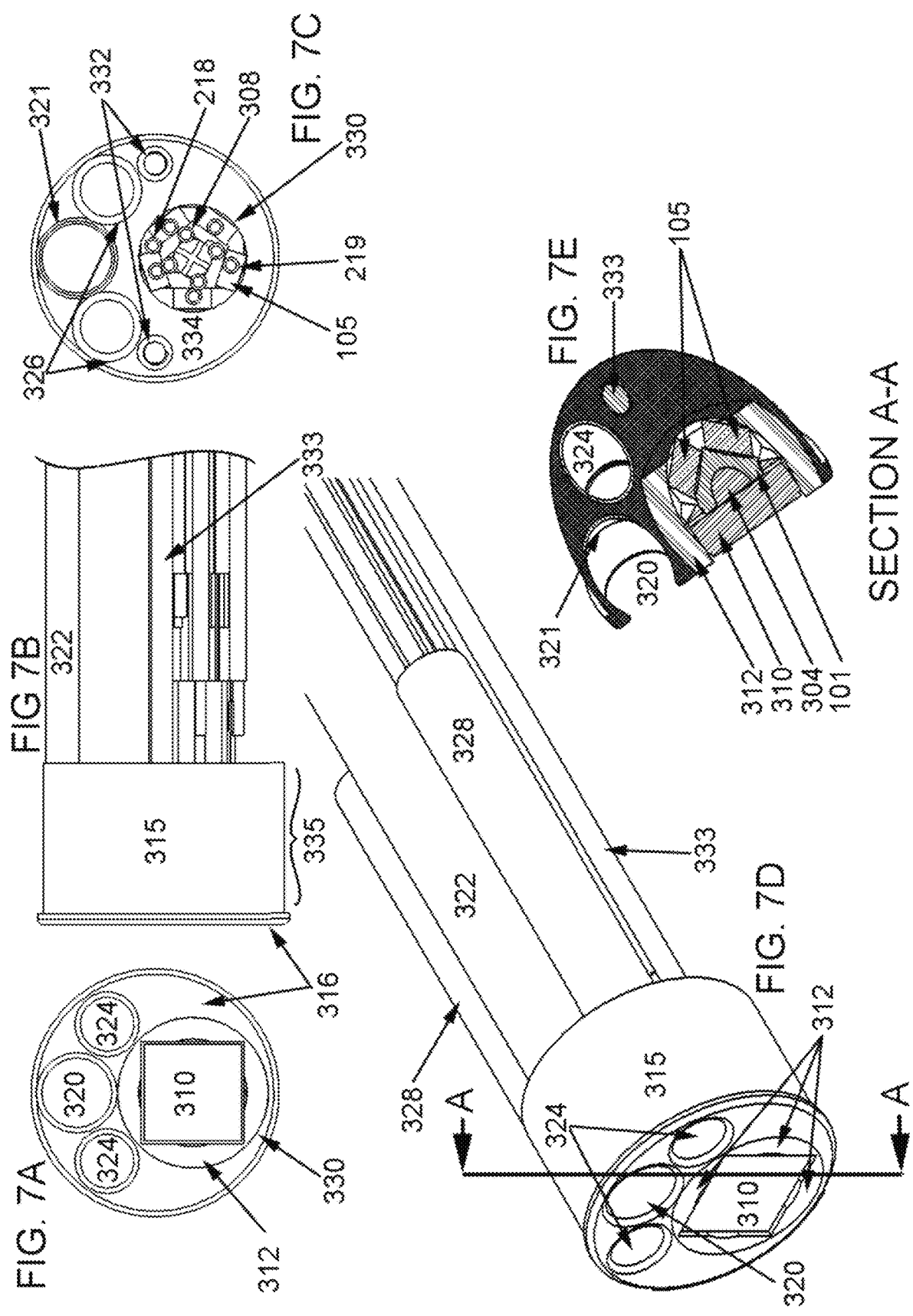

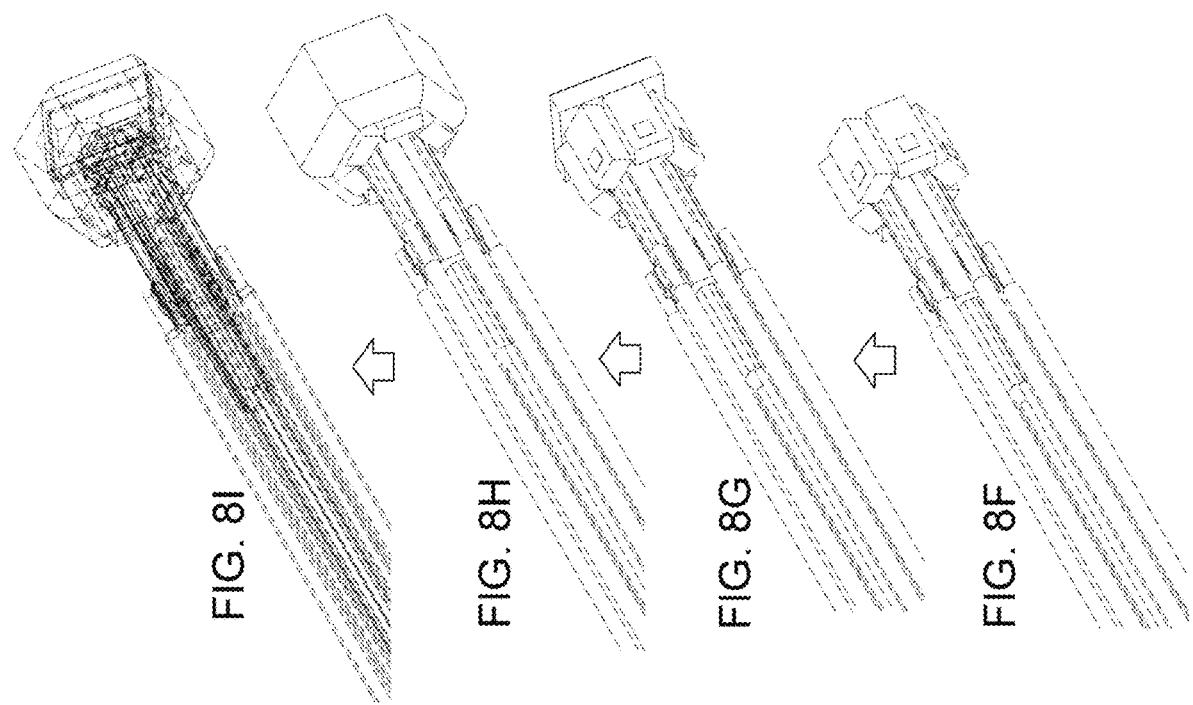
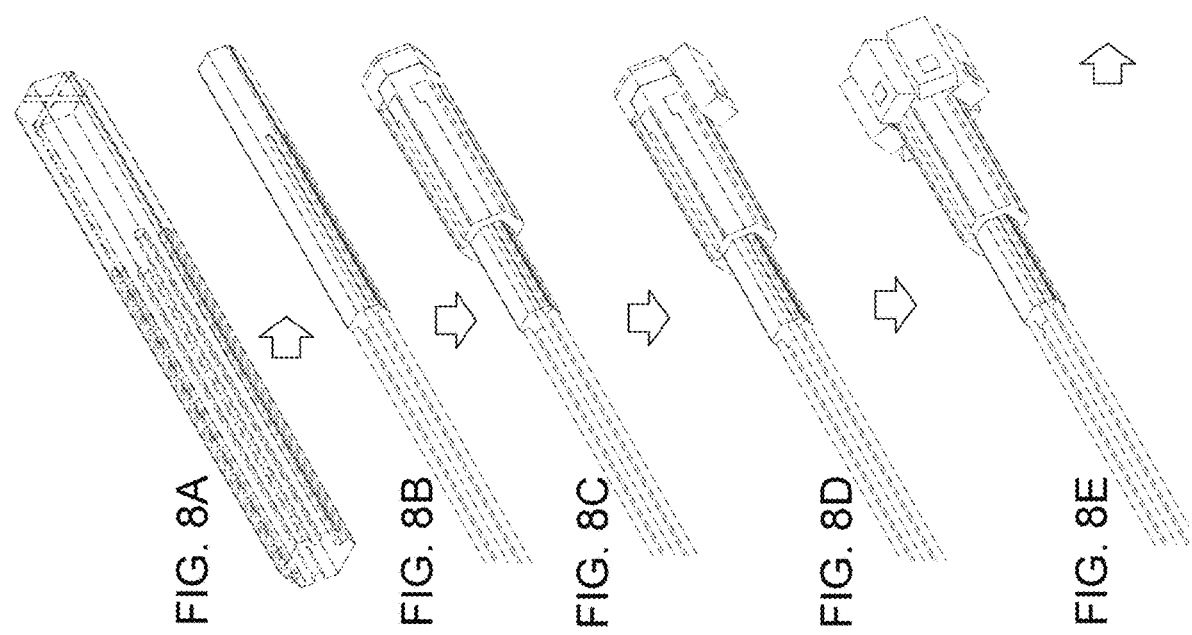

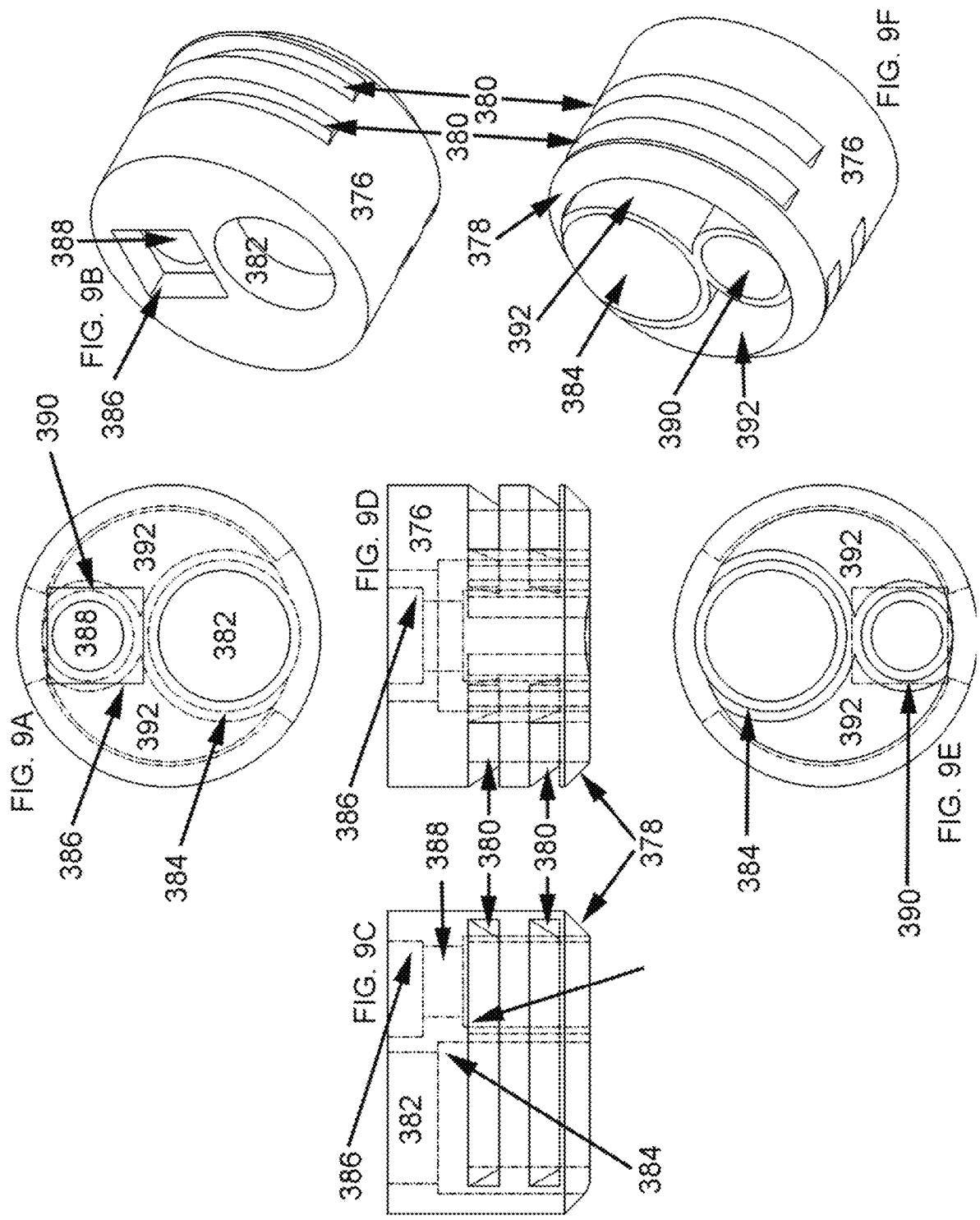

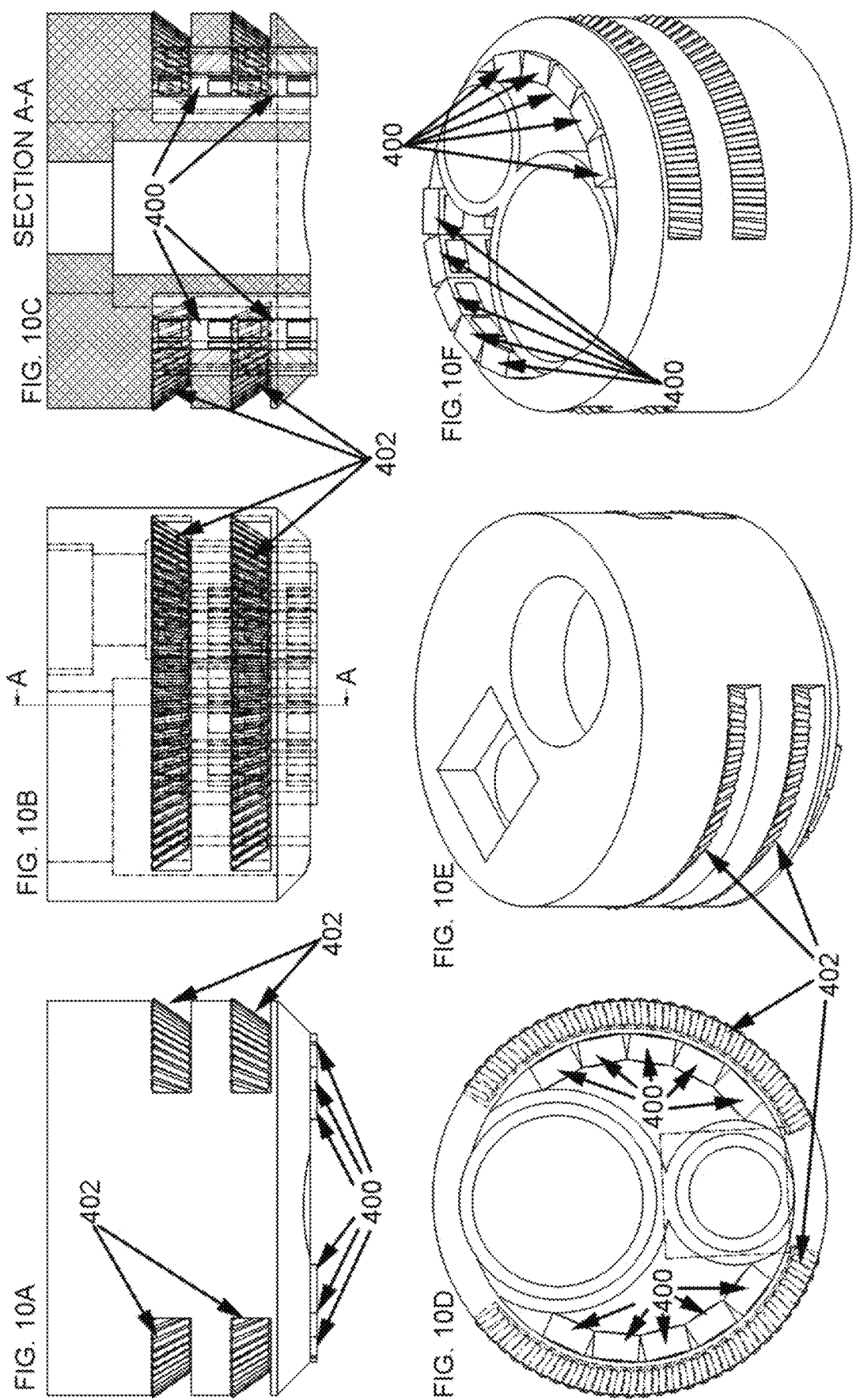

MULTI-SPECTRUM RING ILLUMINATED SURGICAL CAMERA

CROSS-REFERENCE TO RELATED APPLICATIONS

This disclosure claims the benefit of priority to U.S. patent application Ser. No. 16/157,478, filed Oct. 11, 2018, which is incorporated herein in its entirety.

FIELD OF THE INVENTION

Embodiments of the present invention generally relate to small semiconductor imaging devices and illumination provided therefore, as may have utility in medical devices and medical catheters with imaging capabilities, borescopes and other devices for imaging in remote locations via narrow openings and channels.

BACKGROUND

A challenge for the minimally invasive exploration and treatment of internal areas of the human anatomy continues to be adequately visualizing the area of concern. Visualization can be especially troublesome in minimally invasive procedures in which small diameter, flexible and elongate instruments, such as catheters, endoscopes, or more specifically, ureteroscopes and duodenoscopes (herein, all are classified as surgical scopes), are navigated through natural passageways of a patient to an area of concern, either in the passageway or in an organ accessible through the passageway.

A common example is flexible ureteroscopy. Ureteroscopy involves procedures that are used to diagnosis and treat urinary tract diseases such as urinary calculi and ureteral strictures. An ureteroscope is inserted through urethral opening and threaded along the urinary tract, into the bladder, through the ureteral opening and into the kidney calyx. Diagnosis and/or treatment occur under direct visualization as classically provided by fiber optic coupled to imaging systems and light sources. Tiny cameras and light emitting diodes (LEDs) have been exploited in modern ureteroscope design. FIG. 1 depicts a modern ureteroscope tip.

Ureteroscopes are typically 3 mm to 4 mm (10 Fr. to 13 Fr.) in diameter 5 and include a sheath (not shown, coupled to a step on tip outer diameter 65) that encapsulates a fiber optic element (imaging bundle) or imaging chip 15/20 (sensor/substrate) and wiring 55, a fiber optic illumination element (illumination bundle) or LED 30/35 (sensor/substrate) and a working channel 60. Wires are connected via contacts 40/45 (LED/sensor) located upon the substrate 35/20 (LED/sensor). Windows 10/25 (sensor/LED) typically seal the chips from exposure to surgical irrigants.

The working channel (aka "forceps channel") 60 is a lumen for instrument access to tissue through the distal tip of the scope, permitting passage of devices, such as guidewires, optical fibers for delivery of laser energy and stone retrieval baskets. The working channel 60 is also used for introducing sterile irrigant. Drainage of irrigant and surgical detritus typically occurs about the outer diameter of the scope, usually housed within an "access sheathe". Irrigation flow is partially occluded by instruments within the working channel 60, and inadequate flow may allow surgical detritus to build up and impair visualization during surgery. Larger working channels are preferred for both permitting larger instruments to be employed in surgery and for maintenance of a clear surgical field. For reference, in the prior art tip illustrated in FIG. 1, the total tip diameter is 3.2 mm and the working channel is 1.1 mm.

Illumination is typically provided via an optical fiber bundle, terminated within the distal tip of the scope, transmitting light from a source outside of the body. Quite recently, LEDs 30/35 have been used to replace the fiber bundle. Visualization is afforded via an imaging optical fiber bundle or, beginning roughly 20-years ago, via a camera chip 15/20 (sensor/substrate) at the distal tip. Most ureteroscopes also incorporate a steering mechanism (not shown), which allows the distal tip of the scope to be deflected in one or more planes to follow the natural lumen with minimal trauma.

Size is of primary importance for minimally invasive imaging and access devices. Larger diameter devices are typically less flexible (less "steerable"), cannot pass smaller lumen (e.g. in pediatrics) and induce more trauma than smaller devices while themselves suffering damage in forced passage. Larger devices do offer competing advantages, such as permitting larger working channels that provide better irrigant flow and access for larger instruments, but smaller, more flexible devices are clearly favored.

Another compromise made in prior art imaging scopes is the amount and quality of the lighting provided. Fiber optic bundles for lighting are kept small in total diameter and use very small core optical fibers, uncoated, to minimize ureteroscope stiffness and overall diameter; a single fiber bundle or LED 30/35 is typically used and is positioned to one side of the imaging element, providing uneven illumination of the visual field, particularly where that filed is complex in topography.

It would be useful to provide a small diameter, flexible ureteroscope or duodenoscope or similar device that provides superior illumination and visualization within as compact a package as possible.

SUMMARY

In accordance with aspects of the present invention, a small diameter imaging and illumination system is provided. The system is comprised of an imaging "chip" (sensor element, substrate, electrical contacts and interconnects), a plurality of lighting "chips" and a "ring lens" coupling and guiding the light emission from the lighting chips for uniform emission about the imaging chip. Various embodiments are disclosed with principal application being in medical endoscopy and industrial inspection.

A first embodiment is a ring illuminated surgical camera which includes a ring lens that includes an emission surface adjacent to a distal end, a reflector, an external surface, and a proximal void adjacent to a proximal end; a plurality of light emitting diodes (LEDs) carried within the proximal void, adjacent to an internal surface of the ring lens, and adapted to radially emit light, the plurality of LEDs includes a first wavelength LED, a second wavelength LED, and a third wavelength LED; and a grey-scale image capture sensor adjacent to the emission surface and having imaging sensor electrical contacts electrically connected to an array contact post which extends longitudinally through the ring lens.

A second embodiment is ring illuminated surgical camera which includes a ring lens composed of a unitary piece having at a proximal end a reflector, at a distal end an emission surface, and a longitudinal axis running from the proximal end to the distal end; a plurality of LEDs adjacent to an internal surface of the ring lens, the LEDs positioned to radially transmit light into the ring lens wherein the reflector is adapted to reflect the light longitudinally, the plurality of LEDs adapted to emit light at a three to twelve different wavelengths; an grey-scale image capture sensor recessed into the ring lens; the image capture sensor in electrical contact with an array contact post which extends longitudinally through the ring lens.

A third embodiment is a ring illuminated surgical scope which includes an endoscopic cannula affixed to an endoscopic tip; and a plurality of guidewires adapted to affect the orientation of the endoscopic tip; where the endoscopic tip includes a ring illuminated surgical camera which includes a ring lens having at a proximal end a reflector, at a distal end an emission surface, and a longitudinal axis running from the proximal end to the distal end; a plurality of LEDs adjacent to an internal surface of the ring lens, the LEDs positioned to radially transmit light into the ring lens wherein the reflector is adapted to reflect the light longitudinally, the plurality of LEDs adapted to emit light at a three to twelve different wavelengths; an grey-scale image capture sensor recessed into the ring lens; the image capture sensor in electrical contact with an array contact post which extends longitudinally through the ring lens; wherein the emission of light from the plurality of LEDs is adapted to provide separate emissions of each different wavelength and emissions of a plurality of wavelengths.

A fourth embodiment is an in vivo imaging process that includes positioning a ring illuminated surgical camera having a plurality of LEDs adapted to emit light at three to twelve different wavelengths via a ring lens, and a grey-scale image capture sensor recessed into the ring lens, proximal to an in vivo imaging target; actuating the plurality of LEDs to emit light at the different wavelengths and capturing grey-scale images of the in vivo target illuminated at different wavelengths; and processing the captured grey-scale images to provide a multi-spectrum image of the in vivo imaging target.

BRIEF DESCRIPTION OF THE FIGURES

For a more complete understanding of the disclosure, reference should be made to the following detailed description and accompanying drawing figures wherein:

FIG. 1 presents an isometric view (FIG. 1A) and a bisected view (FIG. 1B) of an endoscopic system;

FIG. 3 shows a plurality of views and expanded views of a ring illuminated surgical camera, where FIG. 3A shows a side-on view, FIG. 3B shows a head-on view, FIG. 3C shows a bisected view running along a longitudinal axis (the bisect shown in FIG. 3B as the line A-A), FIG. 3E is an expanded view of Detail B shown in FIG. 3C, and FIG. 3D is an expanded view of Detail C in FIG. 3E;

FIG. 5 shows a plurality of views and expanded views of a square, ring illuminated surgical camera where FIG. 5 A shows on end-on view, FIG. 5B shows a transparent side view, FIG. 5C shows a rear view of with the LED support removed but the LEDs remaining, FIG. 5D shows a transparent orthogonal projection depicting the path of light from the LEDs to the emission surface, and FIG. 5E shows an expanded view of Detail A in FIG. 5C;

FIG. 6 shows a stepwise assembly of a ring illuminated surgical camera and leads, where FIG. 6A shows the contact post and camera leads, FIG. 6B shows the contact post fitted into the LED support which is carrying LEDs and a ring lens, and FIG. 6C shows the LED contacts connected to the LED support;

FIG. 7 shows a plurality of views of a ring illuminated surgical camera incorporated into an endoscopic device where FIG. 7A shows an end-on view of the endoscopic device's tip with working channels, FIG. 7B shows a side view of the endoscopic tip, FIG. 7C shows a rear view of the endoscopic tip with guide wire contact posts and electrical leads, FIG. 7D shows an orthogonal projection of the endoscopic tip, and FIG. 7E shows a bisected, off-axis view of the endoscopic tip (the bisect shown in FIG. 7D as the line A-A);

FIG. 8 shows a stepwise construction of a ring illuminated surgical camera starting from the camera contact post in FIG. 5A, adding camera leads in FIG. 8B, adding the LED support in FIG. 8C, adding a first LED in FIG. 8D, adding additional LEDs in FIG. 8E, adding LED leads in FIG. 8F, adding a camera in FIG. 8G, and adding a ring lens in FIG. 8H, where FIG. 8I is a transparent orthogonal projection of the ring illuminated surgical camera;

FIG. 9 shows a plurality of views of a working-channel ring lens useful in a ring illuminated surgical camera, where FIG. 9A shows an end-on view, 9C shows a first side view, FIG. 9D shows a second side view, and FIG. 9E shows a rear view of the working-channel ring lens, and where FIG. 9B shows an orthogonal front projection and FIG. 9F shows an orthogonal rear projection of the working-channel ring lens;

FIG. 10 shows a plurality of views of a working-channel ring lens useful in a ring illuminated surgical camera, where FIG. 10A shows a side view of the ring lens, FIG. 10B shows a transparent side view of the ring lens, FIG. 10O shows a bisected view of the ring lens (the bisect shown in FIG. 10B as the line A-A), FIG. 10D shows an rear view of the ring lens carrying LEDs, FIG. 10E shows a top-down orthogonal view of the ring lens, and FIG. 10F shows a bottom-up orthogonal view of the ring lens carrying LEDs;

While specific embodiments are illustrated in the figures, with the understanding that the disclosure is intended to be illustrative, these embodiments are not intended to limit the invention described and illustrated herein.

DETAILED DESCRIPTION

Objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Herein, the use of the word "a" or "an" when used in conjunction with the term "comprising" in the claims and/or the specification may mean "one," but it is also consistent with the meaning of "one or more," "at least one," and "one or more than one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

Herein are provided components for and a structure of a ring illuminated surgical scope. The components and structure include a Ring-Illuminated Surgical Camera (RISC) that features at least one light emitting diode (LED), a ring lens, and an electronic imaging sensor. The components and structure provide circular or ring illumination of an optical target thereby allowing the user to clearly image/see the optical target. Importantly, the organization of the LED, ring lens, and imaging sensor in the RISC decrease the cross-sectional diameter of a surgical scope while providing improved diagnostic or surgical capabilities.

A first embodiment of a RISC includes one or more LEDs positioned behind, rather than in plane with, an electronic imaging sensor. Herein, the terms electronic imaging sensor, camera, and camera array mean an electronic device that is adapted for the conversion of light to electrical signals that can be converted back to an image. Examples of such electronic devices include CMOS sensors and CCD sensors.

Figure 2A:
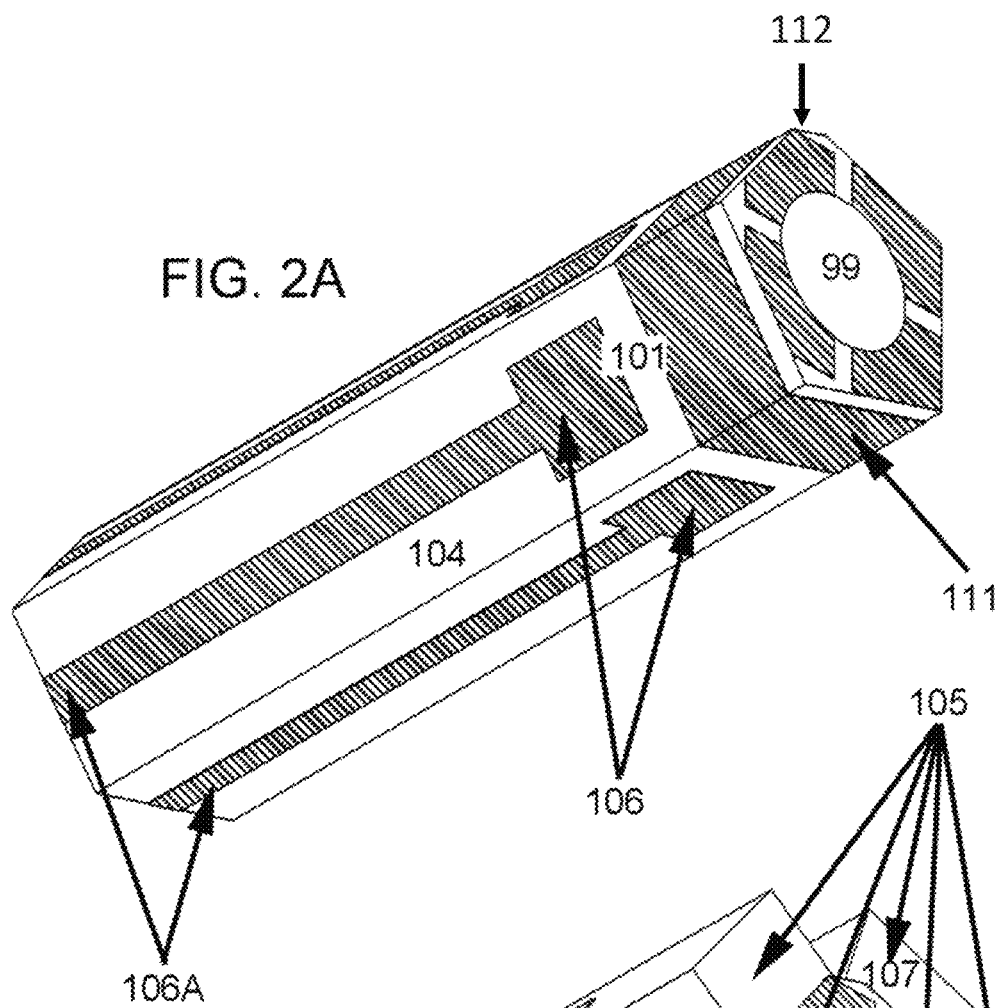
FIG. 2 shows a LED stack with exposed electrodes (FIG. 2A, the LED support) and with affixed LEDs (FIG. 2B)
Figure 2B:
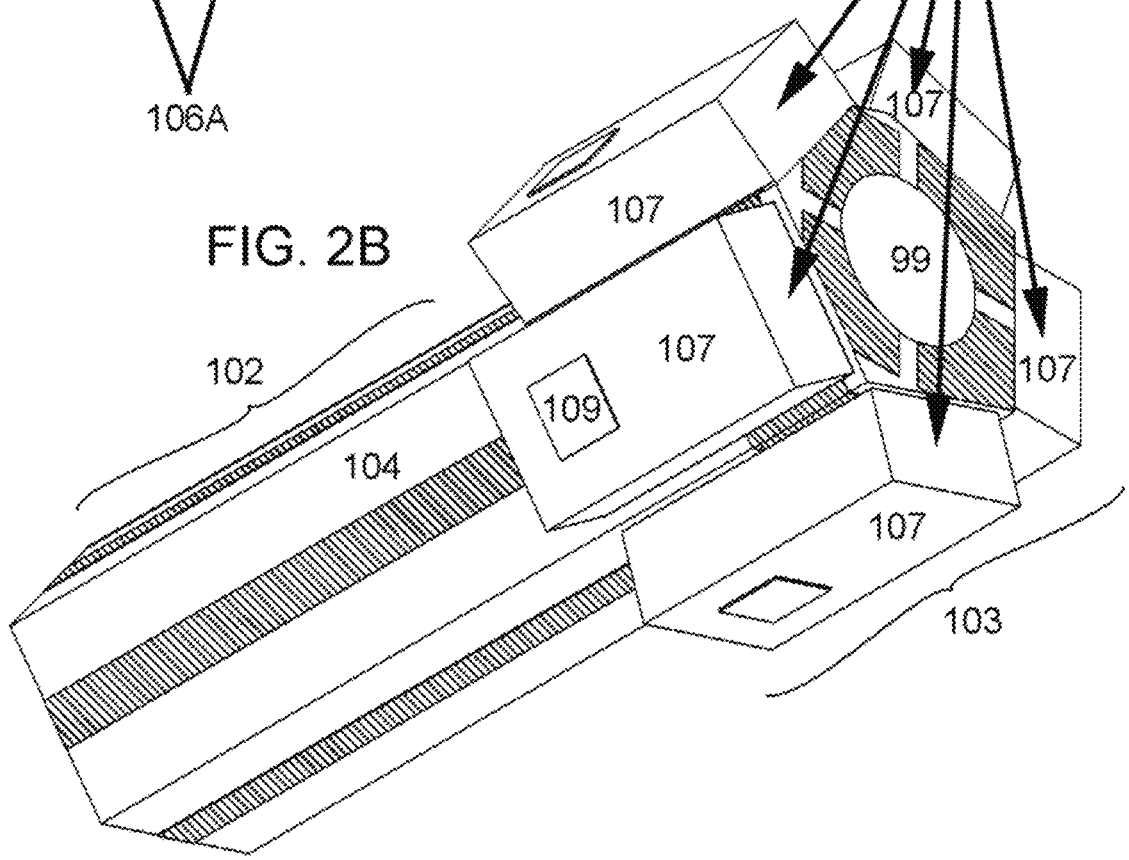

With reference to FIGS. 2 (A and B), herein is provided a compact arrangement of a plurality of LEDs 105, each having a LED emitter 109 upon the substrate 107 and positioned behind and nonparallel with an imaging sensor (not shown). The LED stack 100 includes an LED support 101 and affixed thereto a plurality of LEDs 105. The LED support 101 (FIG. 2A) includes a plurality of support faces 104 each carrying at least one LED power contact 106 and a length of a common return contact 111. The LED support 101 can have 3, 4, 5, 6, 7, 8, 9, or 10 support faces 104, that is, the LED support can have a triangular, square, pentagonal, hexagonal, heptagonal, octagonal, nonagonal, or decagonal cross-section. While additional support faces are possible (in excess of 10), the LED support 101 is preferably sufficiently narrow to allow for use in surgical scopes. Preferably, the LED support 101 has a square, pentagonal, or hexagonal cross-section; that is, the LED support 101 preferably has 4, 5, or 6 support faces 104. Each support face, preferably, further includes at least one LED contact 106 electrically connected to an LED lead 106A and a LED return/common/ground or common LED ground 111. The common LED ground 111 can be carried across a plurality of support faces 104. In certain instances, the LED support 101 can have a plurality of support faces 104 and a LED ground face 112. The LED ground face 112 can have the same dimensions as a support face 104 or can have a more narrow width (whereas the length is preferably the same as the support faces). For example, FIG. 2A depicts an irregular hexagonal cross-section where the LED support 101 has five (5) common faces and a narrower LED ground face 112. When the LED support 101 has a LED ground face 112 the common LED ground 111 is preferably carried across each support face 104 and the LED ground support face 112 (e.g., wrapped around the LED support 101). In a common instance, the LED contact 106, the LED lead 106A, and the common LED ground 111 are composed of a conducting metal, preferably copper, silver, or gold.

The LED support 101 preferably carries at least one LED 105 on each support face 104. Each LED 105 has a LED emitter 107. The LED emitter 107 (or chip or die) commonly has a flat or planar surface and emits light perpendicular to the planar surface (primary emission direction). Preferably, this primary emission direction is nonparallel to the LED support 101 longitudinal axis. More preferably the LED emitter 107 (herein defined by its planar surface) is preferably planar with the support face 104 upon which the LED 105 is affixed. Each LED 105 is preferably affixed (e.g., soldered) to a LED contact 106 and a LED ground 111.

In another instance, the LED support 101 includes a proximal region 102 and a distal region 103. Preferably, the LEDs 105 are carried on (affixed to) the distal region 103 with the LED leads 106A extending to the proximal region. The distal region 103, preferably, includes the LED contacts 106 and the common LED ground 111.

In reference to FIG. 3, each LED 105 can further include a lens or a shaping lens 108 carried or covering the LED emitter 107 and the LED emitter's emission face 109. Preferably, the lens 108 directs light (emissions) from the LED 105 into a ring lens 201 positioned about the LED support 101 and the LEDs 105. As depicted in FIG. 3E, light (large arrows) from the LEDs 105 travels from the emission face 109, through the lens 108, into the ring lens 201. Preferably, the ring lens 201 is adapted to reflect or redirect the light from the LED 105 to and out of an emission surface 202. In one instance, the ring lens 201 includes a ring-shaped body; notably, while the lens is a ring lens, the lens is not required to possess circular symmetry. The ring lens 201 can be circular or possess the same number of sides as the LED support 101. In one preferable instance the ring lens is circular. The ring lens preferably includes an internal surface 204, an external surface 208, a reflector surface 203, and an emission surface 202. In operation, light entering the ring lens 201, preferably, transmits through the internal surface 204, to the reflector surface 203, and exits the ring lens 201 through the emission surface 202. In one instance, the reflector surface has an internal 205 and external 206 components (or surfaces). The reflector surface 203 is angled relative to the internal surface 204 (or the longitudinal axis of the LED support 101). The reflector surface can be at an angle 207 of about 35° to about 55°. In one instance, the reflector surface is angled to provide a total internal reflectance (TIR) of light from the LED 105 to the emission surface 202. In another instance, the reflector surface (the external component 206), ring lens internal surface 204 and ring lens external surface 208 can be mirrored to improve the reflectance and redirection of the light within the ring lens 201. The device includes a plurality of LEDs, the emissions can blend producing uniform illumination about a camera array 301.

Figure 4:
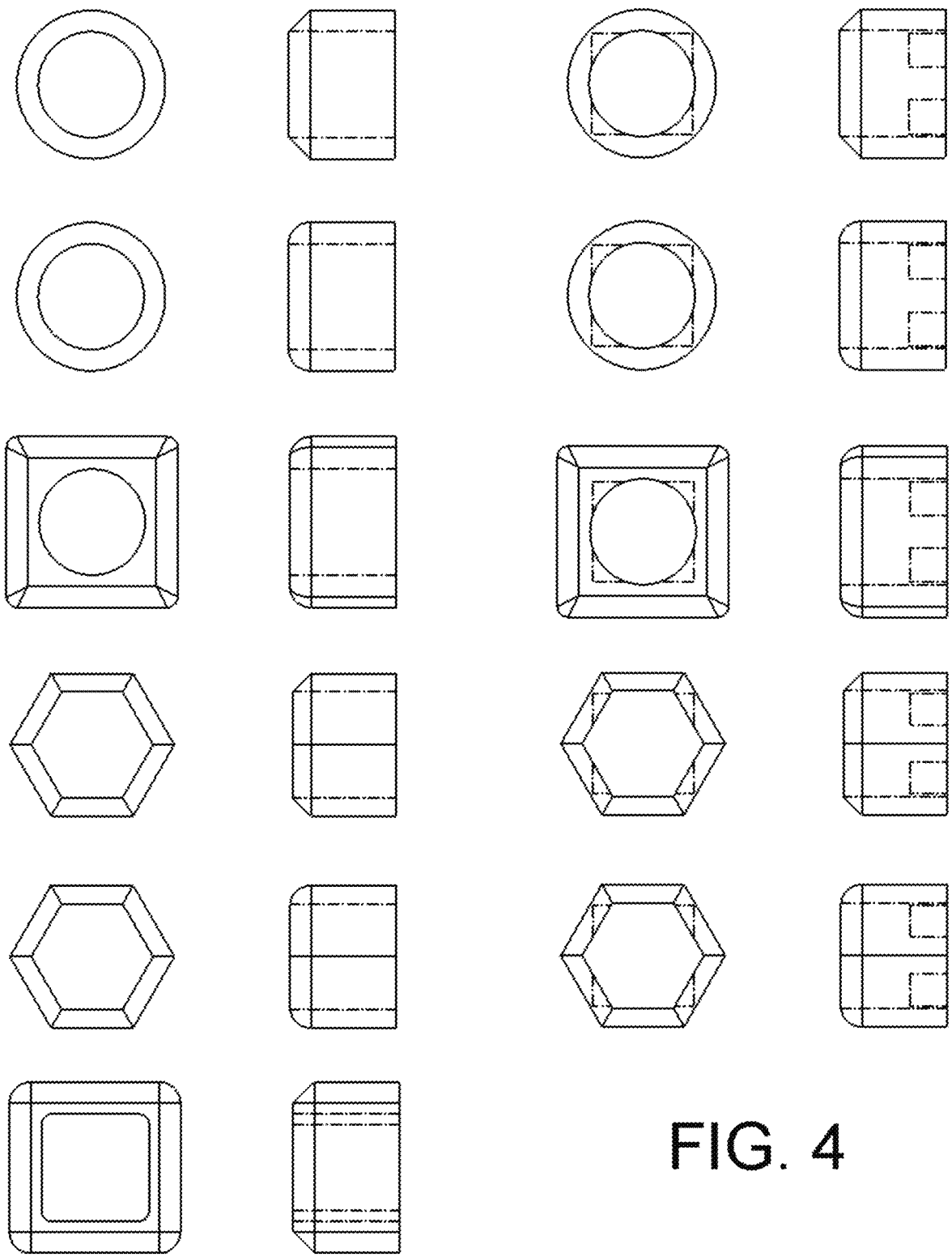
FIG. 4 depicts a series of ring lenses having a variety of shapes, chamfered or filleted geometries, and recesses for carrying an imaging element.

In another example, FIG. 4 the ring lens can have a cross-section that is round, square, pentagonal, or hexagonal. In these examples, the ring lens can have a camera countersink (adapted to carry the camera array). Notably, the proximal end of the ring lens can have a chamfered or filleted geometry. In one instance, the ring lens includes an external surface that is mirrored. In still another example, the ring lens includes an emissions face (where the light from the LEDs exits the ring lens). In a preferable example, the emissions face can be planar. In other examples, the emissions face can be convex, concave, convex conical, or concave conical. Notably, the selection of the orientation of the emissions face can be dependent on the number of LEDs, the focal point of the LEDs and the camera array, and any tools that are used in a surgical space. In a preferably example, the ring lens is a unitary piece of fused silica or quartz.

FIG. 5 depicts another example of the RISC without showing the LED support or the imaging contact post. In this example, the ring lens 312 has a square profile. Furthermore, in this example, the ring lens does not include a countersink, but the inside diameter of the ring lens is approximately the same diameter of the camera array, for example, within about 0.01, 0.02, 0.03, 0.04, 0.05, 0.06, 0.07, 0.08, 0.09, or 0.1 mm of the diameter of the camera array. Here, the camera array 310 rests within the open internal cross-section (lumen, meaning the inside space of a tubular structure) 336 of the ring lens 312. The camera array can be set back (proximal) beneath a window 314 used to seal the sensor space and protect its surface. In another instance, the camera array can be flush with the emission surface of the ring lens. In yet another instance, the ring lens 312 and the window 314 can be a single piece of transparent material, e.g. fused quartz, fused silica, sapphire, polymer, crown glass, where the volume for the camera array is provided within the single piece of transparent material.

The camera array 310 can include a chip 337 and a substrate 338 upon the proximal side of which are provided camera electrical contacts 340. The camera electrical contacts 340 are preferably in electrical contact the electrical contacts 305 for the camera array, or traces 215 (FIGS. 6A & FIG. 6B), carried on the contact post 304 (FIG. 6A). In one instance, the chip 337 (or chip face) is adjacent to, or in contact with the window 314.

As shown in FIG. 5, the RISC can include a plurality of LEDs wherein the plurality of LEDs can be grouped or individually distinct by wavelength or wavelength range. FIG. 5C depicts eight LEDs in two groups of four (350 and 365). Preferably, the RISC includes at least 3, 4, 5, or 6 "white" light LEDs 350 symmetrically placed about the ring lens 312. Herein, symmetrically placed can mean that there is a rotational axis along the longitudinal axis. Preferably, symmetrically placed means that when the "white" light LEDs are actuated and providing illumination about the camera array, the resulting projected light is symmetric. The RISC can further include auxiliary LEDs 365 that can provide light in one or more colors. Preferable examples include providing blue or red light to accentuate blood vessels, UV light to stimulate fluorescent dyes, or light of different color temperatures to provide alternative lighting or contrast when the surgical field is viewed via the camera array.

FIG. 5D depicts light (large arrows) exiting the LED emitters 344, entering the ring lens 312, being reflected by the angled TIR or mirror surface 360, and then exiting about the camera sensor 310. In contrast to prior art, such arrangements provide several fold more light in the surgical field and that light is far more uniformly distributed about the imaging element while requiring less space within the endoscope tip than other arrangements.

In another instance, the LED support includes a bore 99 (FIG. 2) or pathway from the proximal end to the distal end through which an imaging contact post 304 (FIG. 6) can be passed, preferably without contacting the LED contacts 106 or LED leads 106A. Preferably, the imaging contact post 304 fits the bore though the LED support 101, that is has approximately (within about 0.05 mm) the same dimensions as the bore and can be pressed into position during assembly. In another instance, the bore and the contact post 304 have a cross section that is similar or the same as the LED support 101, e.g. square, pentagonal, or hexagonal. In one preferable instance, the contact post 304 has a square cross-section. In another preferable instance, the contact post 304 is cylindrical.

FIG. 6 depicts the LED support 101 carrying the ring lens 201 with the contact post 304 and shows the electrical contacts for both the LED and the camera array. The electrical contacts for the camera array, or traces 215, are preferably carried on the face 307 of the contact post 304. As shown in FIG. 6A, the contact post carries both the traces 215 and camera conductors 308. The camera conductors 308 are in electrical contact with the traces 215, preferable are affixed to the traces 215, more preferably are soldered 306 to the traces 215. The conductors 308 can be standard electrical wires or a bundle of insulated wires fitted about at least a portion of the contact post 304 or coaxial shielded cable. FIG. 6B depicts the contact post 304 fitted within the LED support 101, preferably with a minimum distance of about 0.1, 0.2, 0.3, 0.4, 0.5, 0.6, 0.7, 0.8, 0.9, or 1 mm between the proximal end of the LED support 101 and the terminus of the camera conductors 308.

Another instance includes wiring for the LEDs 105. As shown in FIG. 6C, an LED conductor 219 is preferably in electrical contact with, more preferably affixed to, even more preferably soldered to a LED lead 217 (106A in FIG. 2). In one example, there is one LED conductor for each LED 105; in another example, there is wiring such that the LEDs 105 are in series or in parallel. In either example, a complete circuit requires a ground (return). Preferably, a common conductor 218 is in electrical contact with, more preferably affixed to, even more preferably soldered to the common LED ground 220 (111 in FIG. 2). In another instance, each LED 105 (FIG. 2) can be in electrical contact with a ground, or a plurality of LEDs 105 can be in electrical contact with a single ground. Preferably, there is one LED conductor 219 for each LED lead 217, thereby providing a means for individually and selectively activating (actuating/illuminating) each LED. A proximal end-on view of the arrangement of the LEDs 105, LED conductors 219, common conductor 218, and the camera conductors 308 is depicted within FIG. 7C.

In another instance, the RISC features the LEDs 105, LED support 101, the camera contract post 304, and the camera array 310, with the leads and grounds carried by the LED support 101 and the contact post 304. The RISC can then further include the LED conductors 219, common conductor 218, and the camera conductors 308 each in electrical contact with the LEDs, leads, grounds, or camera array. Alternatively, the RISC can include a ring light that features the LEDs 105 and the LED support 101 (as shown in FIG. 2) and a camera component that includes the camera array 301 and the contact post 304.

FIG. 7 further shows features and elements of the working end of an endoscope that includes a RISC. In one example, the scope tip body 315 includes at least one counter bore recesses (in the scope tip face 316) for mounting a RISC. The scope tip body 315 can further includes a working channel port 320 and counter bore 321 for mating the working channel liner 322, an auxiliary port 324 and counterbore 326 for mating with a conduit 328 (for example, for use in continuous flow irrigation or other needs), a RISC bore 330 for mounting the RISC assembly as depicted in FIG. 3; and a turned down region 335 having an exterior diameter for mating with an endoscopic outer sleeve/cannula (not shown).

In one embodiment of the RISC, the camera array can be square (most commonly the camera array is square due to the 2-dimensional grid design of the detecting elements, other shapes can be imagined). In one instance, the camera array is counter sunk into the ring lens. That is, the face of the camera array can be flush with the emission surface 202 of the ring lens. In another instance, the face of the camera array can extend beyond the emission surface 202 of the ring lens 201 (FIG. 3). In one example, the camera array is seated on the ring lens, in another example the camera array is within the internal diameter of the ring lens. FIGS. 5A and 5D depict a square, camera countersink 310 in the ring lens 312. In this example, the lens ring 312 is mounted within the scope tip body 315, with the emission surface 202 flush with the scope tip face 316.

The scope tip body 315 (FIG. 7) can further include steering wires 333 for control of the orientation of the scope tip face 316. The steering wires 333 can be mounted within receiving holes 332 provided on the proximal face 334 of the scope tip body 315. Notably, FIG. 7A shows an end-on view of the scope tip body 315 (in FIG. 7B) whereas FIG. 7C shows an internal view of the scope tip body 315 (in FIG. 7B) as seen from the proximal end. Preferably, the steering wires and mounted to the scope tip body 315 within receiving holes 332 that do not extend through the scope tip body 315 to the scope tip face 316.

FIG. 7E shows a diagonal cross section of the scope tip body 315 depicted in FIG. 7D. Therein, portions of the LED support 101, LEDs 105, and sensor contact post 304 are visible. Other elements described in FIG. 3 may be seen in FIG. 7C for orientation: an LED 105, sensor conductors 308, LED power 219 and common/return 218 conductors.

Figure 11:
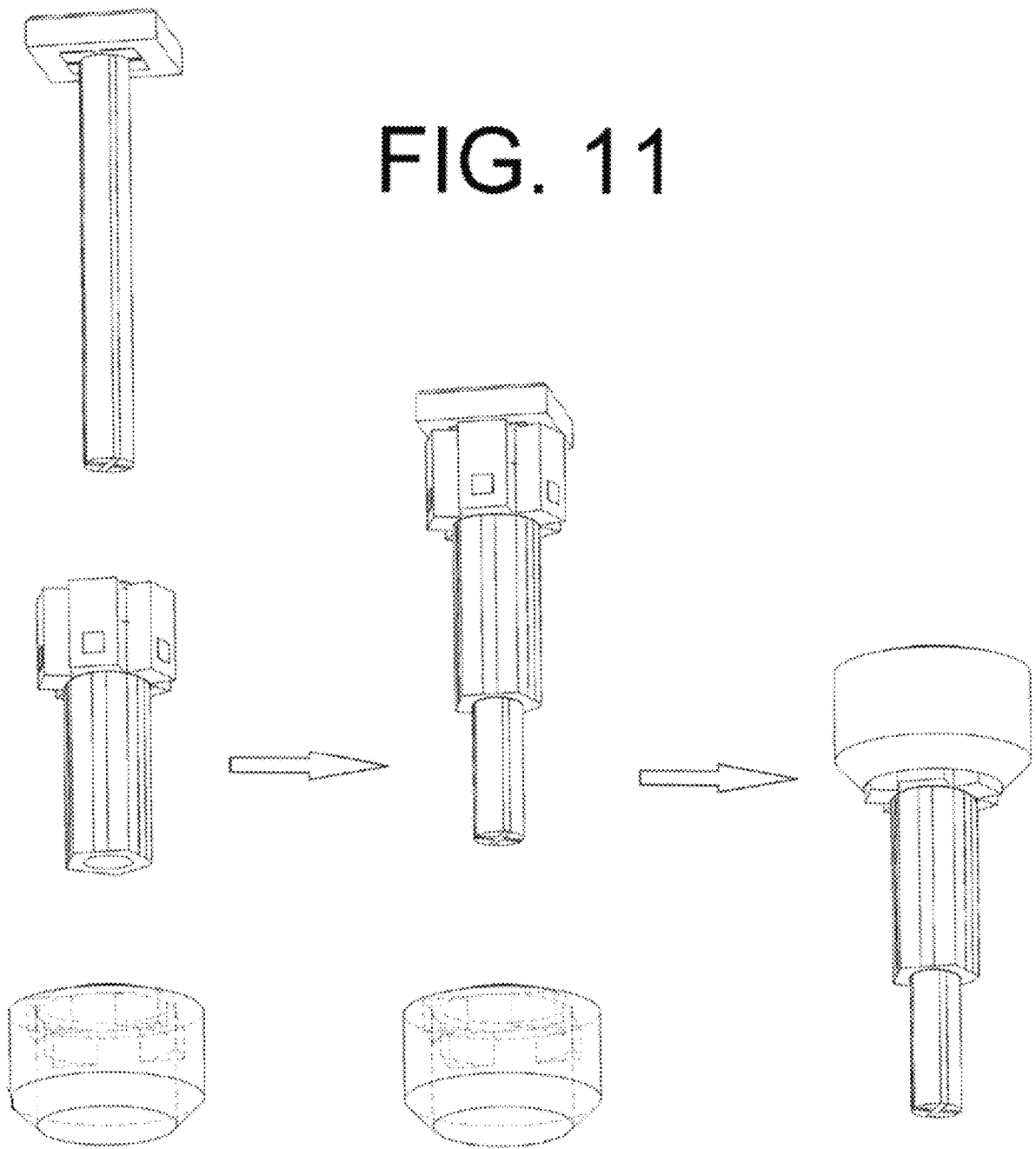
FIG. 11 shows a schematic assembly of a ring illuminated surgical camera, showing a placement of the camera on the camera contact post, the LED support carrying the LEDs, and the ring lens.

FIG. 8 shows another embodiment wherein the ring lens is hexagonal, illustrating a means for build-up of the RISC assembly. Notably, FIG. 8 shows a layer by layer arrangement of a ring illuminated surgical camera starting from the camera contact post in FIG. 8A. Then, in FIG. 8B, camera leads are shown added to the camera post. Then the LED support in FIG. 8C is shown over the camera post. Next, in FIGS. 8D and 8E, LEDs are shown affixed to the LED support. Then, in FIG. 8F, LED leads are shown connected to the LED support. In FIG. 8G, the electronic imaging sensor (camera) is shown in relation to the LEDs. FIG. 8H now shows the ring lens (a hexagonal ring lens) about the LEDs and electronic imaging sensor. Finally, FIG. 8I shows a transparent orthogonal projection of the ring illuminated surgical camera. Notably, the assembly of the ring illuminated surgical camera can follow the order shown in FIG. 8 or can follow an order determined by the means of assembly. In one notable instance, the electronic imaging sensor is added after the ring lens. In another instance, the leads are added after the assembly of the LED support, LEDs, camera post, and ring lens. Likewise, FIG. 11 shows and exploded assembly of the ring lens (i.e., a circular ring lens), the LED support carrying LEDs, and the camera post carrying the electronic imaging sensor.

A further embodiment of the ring illuminated surgical camera includes a LED support including a proximal region, a distal region, a plurality of external faces extending from the proximal region to the distal region, and a longitudinal axis extending from the proximal region to the distal region. The RISC further includes a plurality of light emitting diodes carried radially about the LED support and carried upon the external faces of the LED support. Additionally, the RISC includes a ring lens including an emissions face, a reflector, and an internal surface extending longitudinally from the emissions face to the reflector. Preferably, the plurality of light emitting diodes are adjacent to the internal surface of the ring lens. In one instance, the RISC includes 4 to 8 LEDs, in another instance, the RISC includes at least one LED for each common face on the LED support (See the discussion of FIG. 2A which depicts an irregular hexagonal cross-section where the LED support having five (5) common faces). In another instance the RISC include 3-20, 4-16, 5-15, or 6-10 LEDs.

The LEDs are preferably carried on the distal region of the LED support. The LED support preferably includes a plurality of LED contacts, each extending from a LED along an external face of the LED support to the proximal region of the LED support.

In another instance, the LEDs each include a LED emitter having an emitter face, where each emitter face is parallel to the longitudinal axis. That is, the LEDs emit radially about the LED support. Preferably, each LED includes a LED lens carried on the emitter face. That is, the emitter face is covered by a lens element, the LED lens can be flat, convex, concave, semicylindrical, or semispherocylindrical. Preferably, the LED lens is adjacent to the internal surface of the ring lens. More preferably, the LED lens has an external surface that is matched to the internal surface of the ring lens. In one instance, the LED lens can have a semicylindrical surface with a curvature that matched the internal curvature of the ring lens. For example, the internal surface of the ring lens can have an internal radius of curvature; wherein the LED lens has a LED radius of curvature; and wherein the internal radius of curvature is equal to the LED radius of curvature. In another instance, the LED lens can have a flat or plurality of flat surfaces that match to flat or a plurality of flat internal surfaces of the ring lens. In still another instance, the LED lens can have any specific shape and the internal surface of the ring lens can be match (cut or formed) to match the LED lens external surface.

In yet another instance, each LED has a LED optical axis. Herein the LED optical axis is the primary direction of emission from the LED, the optical axis is typically perpendicular to the LED chip face. Preferably, the LEDs are positioned relative to the ring lens such that a LED optical axis bisects the reflector.

The reflector preferably reflects light emitted from the LED and redirects the light to the emissions face. Accordingly, the reflector includes an internal reflection surface (a surface against which the light reflects while within the ring lens). In one instance, the internal reflection surface has a conical angle of about 35° to about 55° (the conical angle is the angle between the reflection surface and the longitudinal axis). Further qualities of the reflector were discussed in reference to FIG. 3, above. Examples of the reflector include an internal reflection surface; wherein the internal reflection surface is mirrored (herein, this means that the reflector is treated to reflect greater than 95%, preferably greater that 99% of incident light; one means for mirroring the reflection surface is the apply a layer of silver); or wherein the reflector includes an internal reflection surface; wherein a side of the internal reflection surface distal from the internal surface carries a reflective metallic coating. Still further, the ring lens can include an external surface that is mirrored.

In a preferable example, the ring lens includes an emissions face can be planar. In other examples, the emissions face can be convex, concave, convex conical, or concave conical.

In still another example, the ring lens is constructed from surgically acceptable, and optically transparent materials. In one preferably instance, the ring lens is a unitary piece of fused silica or fused quartz. In another instance, the ring lens is a transparent material, e.g. fused quartz, fused silica, sapphire, a polymer, or crown glass. In still another instance, the ring lens is a plurality of hermetically sealed transparent pieces composed of fused quartz, fused silica, sapphire, a polymer, and/or crown glass.

The RISC can further includes an electronic imaging sensor (camera) that includes an imaging array and imaging sensor electrical contacts; an array contact post including a proximal region, a distal region, an external face extending from the proximal region to the distal region, and a longitudinal axis extending from the proximal region to the distal region that is parallel to and coincident with the LED support longitudinal axis, with the imaging sensor electrical contacts adjacent to the array contact post distal region; and a plurality of array contacts in electronic communication with the imaging sensor electrical contracts and extending therefrom to the contact post proximal region. In one instance, the array contact post and the array contacts can pass through the LED support. In another instance, the electronic imaging sensor is carried upon the ring lens. In yet another instance, the electronic imaging sensor is recessed into the ring lens, wherein in one example, the imaging array is coplanar with the emissions face.

Yet another embodiment is a RISC that includes a ring lens having an emission surface, a reflector, and external surface, a lumen defined by an internal surface which extends longitudinally from the emissions face to the reflector, and an electric wire conduit port passing through the emissions face and adapted to carry an electronic imaging sensor and imaging sensor electrical contacts; and a plurality of light emitting diodes (LEDs) carried within the lumen, adjacent to the internal surface of the ring lens, and adapted to radially emit light. The RISC can further include an electronic imaging sensor adjacent to the emission surface; the electronic imaging sensor having an imaging array and imaging sensor electrical contacts. In one instance, the electronic imaging sensor is recessed into the ring lens. In another instance, the imaging array is coplanar with the emissions surface. In yet another instance, the RISC includes an array contact post in electrical contact with the imaging sensor electrical contacts, the array contact post extending through the electric wire conduit port and extending longitudinally through the ring lens. In another instance, the imaging array and imaging sensor electrical contacts are disposed about opposing surfaces of the electronic imaging sensor. In still another instance, the electronic imaging sensor is affixed to the ring lens and a plurality of imaging sensor electrical contacts in electrical contact with the electronic imaging sensor pass through the electric wire conduit port and through the ring lens.

The RISC can further include a LED support including a proximal region, a distal region, a plurality of external faces extending from the proximal region to the distal region, and a longitudinal axis extending from the proximal region to the distal region; wherein the plurality of LEDs are carried radially upon the external faces of the LED support. The RISC with the LED support can further include an array contact post adapted to carry an electronic imaging sensor, the array contact post extending through the electric wire conduit port and extending longitudinally through the LED support.

In another example, the RISC can include a ring lens which includes a working channel port passing through the emissions face, where the working channel port adapted to carry an instrument and/or fluid.

In yet another example, the RISC includes greater than 4, 5, 6, 7, 8, 9, 10, 11, 12, 13, 14, or 15 LEDs. In one instance, the RISC can include 4 to 20 LEDs, 4 to 18 LEDs, 4 to 16 LEDs, 4 to 14 LEDs, 4 to 12 LEDs, or 4 to 10 LEDs. The LEDs can be the same or selected from different emission wavelengths.

Each LED, preferably, includes a LED lens carried on an emitter face; wherein the LED lens is adjacent to the internal surface of the ring lens. In one instance, the LED lens has an external surface that is matched to the internal surface of the ring lens.

The ring lens reflector includes a reflection surface; preferably, where the reflection surface and/or the external surface are mirrored. In another instance, the ring lens includes a plurality of reflectors positioned longitudinally about the ring lens. In still another instance, the ring lens includes a plurality of reflectors positioned radially about the ring lens. In yet another instance, the ring lens includes a plurality of reflectors positioned radially and longitudinally about the ring lens. In yet another example, the ring lens is a unitary piece of fused silica or quartz.

Yet another embodiment is a ring illuminated surgical scope that includes an endoscopic cannula affixed to an endoscopic tip; and a plurality of guidewires adapted to affect the orientation of the endoscopic tip. The endoscopic tip, preferably, includes a ring illuminated surgical camera; the ring illuminated surgical camera includes a ring lens that includes an emission surface, a reflector, and external surface, a lumen defined by an internal surface which extends longitudinally from the emissions face to the reflector, and an electric wire conduit port passing through the emissions face and adapted to carry an electronic imaging sensor and imaging sensor electrical contacts; a plurality of light emitting diodes (LEDs) carried within the lumen, adjacent to the internal surface of the ring lens, and adapted to radially emit light; an electronic imaging sensor adjacent to the emission surface, the electronic imaging sensor having an imaging array and imaging sensor electrical contacts; and a plurality of imaging sensor electrical contacts in electrical contact with the electronic imaging sensor passing through the electric wire conduit port and through the ring lens. The endoscopic tip can further include at least one working channel adapted to provide instrument access and/or fluid flow to a surgical site, preferably, where the working channel passes through the emissions face.

Additional gains in performance within a compact geometry are available through further embodiments. FIG. 9 depicts a one contiguous piece, transparent polymer ring lens 376 that serves more functions than the prior embodiments described. The essentially cylindrical lens and housing element 376 has a chamfered 378 or stepped proximal diameter for mating to catheter tubing, equipped with TIR or reflective material coated, and partially circumferential, light reflectors 380 in the outer diameter of the cylinder, a working channel port 382 that is counterbored 384 to receive a working channel liner (not shown) and an image sensor chip (not shown) recess 386 with an electric wire conduit port 388 that is counterbored 390 for conduit attachment (not shown). The proximal side of the one-piece housing and lens 376 is hollowed out 392 to provide space for staking LEDs (not shown) facing radially outward or at skew angles within the structural voids 392. Deflection control wires would terminate within the metal ring (not shown) that mates to the chamfer 378 or stepped OD. Furthermore and as shown in FIG. 9, the ring lens can include a plurality of reflectors 380. FIG. 9 depicts reflectors positioned radially about the ring lens (i.e., a plurality of reflectors in the same radial plane) and positioned longitudinally about the ring lens (i.e., repeating at a spacing along the longitudinal axis). In the instance shown in FIG. 9, the ring lens can include four reflectors positioned both radially and longitudinally about the ring lens.

LEDs 400 have been added to another embodiment based upon the concepts in FIG. 9, as depicted in FIG. 10, where the one-piece lens housing's reflective surfaces (380 in FIG. 9) have been equipped with light dispersing elements 402. Twenty LEDs 400 in all are stacked within the proximal voids (392 in FIG. 9), with the emitters (not visible) pointed radially outward at the reflectors 380. Uniformity of illumination may be further controlled by adding off radial mounting within the available space 392 and/or divergence altering lenses on the LEDs.

Still further, the RISC can include one or more camera lenses set before the electronic imaging sensor. In one instance, a camera lens can be coplaner with the emission surface of the ring lens. In another instance, a camera lens can be carried above (distal to) the ring lens. In still another instance, the camera lens can be integral to the ring lens; that is, in one example with reference to FIG. 5B, the ring lens can include a window 314 that is adapted to focus light reaching the electronic imaging sensor. Notably, the window 314 can be integral to the ring lens 312 (e.g., one piece of fused silica, quartz, or plastic). In still another instance, the RISC includes a plurality of camera lenses set before the electronic imaging sensor and adapted to focus light onto the sensor. In yet another embodiment, the relative positions of one or more lens can be adjusted (e.g., moved along the longitudinal axis) to affect the focus of light on the sensor.

Still yet further, the structures and orientation of parts described above can be utilized in a multi-spectrum ring illuminated surgical camera (MS-RISC). In one embodiment a multi-spectrum ring illuminated surgical camera can include the ring lens which has an emission surface adjacent to a distal end, a reflector, an external surface, and a proximal void adjacent to a proximal end; and the plurality of light emitting diodes (LEDs) carried within the proximal void, adjacent to an internal surface of the ring lens, and adapted to radially emit light. In the multi-spectrum ring illuminated surgical camera, the plurality of LEDs includes a first wavelength LED, a second wavelength LED, and a third wavelength LED. That is, LEDs which emit light at, at least, three different wavelengths. In one instance, the plurality of LEDs includes a fourth wavelength LED. In still another instance, the plurality of LEDs includes a fifth wavelength LED. The plurality of LEDs can include one LED at each wavelength but preferably includes at least two first wavelength LEDs, more preferably, includes at least two LEDs at each wavelength. In another instance, the plurality of LEDs includes at least one white light LED. In yet another instance, the plurality of LEDs includes at least one LED that emits light in the UV or IR spectrum, preferably, includes at least one LED that emits light in the UV and one LED that emits light in the IR. Individual Wavelengths can be selected from those in the ultraviolet, violet, blue, cyan, green, yellow, orange, red, magenta, and infrared regions of the electromagnetic spectrum.

The multi-spectrum ring illuminated surgical camera further includes grey-scale image capture sensor adjacent to the emission surface and having imaging sensor electrical contacts electrically connected to an array contact post which extends longitudinally through the ring lens. As described more fully above, the image capture sensor can be recessed into the ring lens; and/or can include an imaging array which is coplanar with the emissions surface. Furthermore, the MS-RISC can include a camera lens adjacent to the emission surface and adapted to focus light on the image capture sensor. Preferably, the grey-scale image capture sensor includes a plurality of pixels each having a diameter of or less than about 4 µm, 3 µm, 2 µm, or 1 µm. More preferably, the grey-scale image capture sensor has dimensions of less than 2×2 mm (length×width), less than 1.5×1.5 mm, less than 1×1 mm, less than 0.75×0.75 mm, or less than 0.5×0.5 mm. In still another instance, the grey-scale image capture sensor carries greater than about 50,000 pixels (50 kilopixels or 50 KP), 100 KP, 150 KP, 200 KP, 250 KP, or 300 KP.

As described above, instances of the multi-spectrum ring illuminated surgical camera can include a ring lens which is circular; a reflector having a reflection surface, where the reflection surface and/or an external surface of the ring lens are mirrored; and/or a ring lens which is a unitary piece of fused silica or quartz.

In another embodiment, a multi-spectrum ring illuminated surgical camera can include, as a first part, a ring lens composed of a unitary piece having at a proximal end a reflector, at a distal end an emission surface, and a longitudinal axis running from the proximal end to the distal end. As a second part, a plurality of LEDs adjacent to an internal surface of the ring lens, the LEDs positioned to radially transmit light into the ring lens wherein the reflector is adapted to reflect the light longitudinally, the plurality of LEDs adapted to emit light at three to twelve different wavelengths. As a third part, an grey-scale image capture sensor recessed into the ring lens; the image capture sensor in electrical contact with an array contact post which extends longitudinally through the ring lens. The ring lens, as used herein, can be composed of fused silica, quartz, or glass; or can be composed of plastic.

In a preferable instance, the multi-spectrum ring illuminated surgical camera includes at least two LEDs adapted to emit light at each of the three to twelve different wavelengths. That is, the plurality of LEDs includes at least 6 individual LEDs (when there are two LEDs per wavelength).

In another instance, at least one of the three to twelve different wavelengths is selected from an absorption maxima of a surgical chromophore. The surgical chromophores can be selected from the absorption peaks, the bathochromic shifts, and hypochromic shifts of in vivo materials, where the in vivo materials can be selected from an endogenous chromophores, variants or degradation products thereof, and mixtures thereof.

Yet another embodiment is a multi-spectrum ring illuminated surgical scope. This surgical scope can include an endoscopic cannula affixed to an endoscopic tip and a plurality of guidewires adapted to affect the orientation of the endoscopic tip. In this embodiment, the endoscopic tip includes a multi-spectrum ring illuminated surgical camera. In one instance, the multi-spectrum ring illuminated surgical camera includes a ring lens having at a proximal end a reflector, at a distal end an emission surface, and a longitudinal axis running from the proximal end to the distal end; a plurality of LEDs adjacent to an internal surface of the ring lens, the LEDs positioned to radially transmit light into the ring lens wherein the reflector is adapted to reflect the light longitudinally, the plurality of LEDs adapted to emit light at a three to twelve different wavelengths; and an grey-scale image capture sensor recessed into the ring lens; the image capture sensor in electrical contact with an array contact post which extends longitudinally through the ring lens. In other instances, the multi-spectrum ring illuminated surgical camera is any of those described above. Preferably, the multi-spectrum ring illuminated surgical camera is adapted to provide separate emissions at each wavelength. That is, the multi-spectrum ring illuminated surgical camera is adapted to illuminate at a first wavelength, then at a second, then at a third, and so on; the multi-spectrum ring illuminated surgical camera can further be adapted to illuminate at a plurality of wavelengths (e.g., at the first and the second) or illuminate with a white light. In one example, the emission of light from the plurality of LEDs is adapted to provide separate emissions of each different wavelength and emissions of a plurality of wavelengths.

The multi-spectrum ring illuminated surgical scope can further include working channels or tools. In one instance, the endoscopic tip can include at least one working channel adapted to provide instrument access and/or fluid flow to a surgical site.

Still another embodiment is an in vivo imaging process. The process preferably includes positioning a ring illuminated surgical camera having a plurality of LEDs adapted to emit light at three to twelve different wavelengths via a ring lens, and a grey-scale image capture sensor recessed into the ring lens, proximal to an in vivo imaging target; actuating the plurality of LEDs to emit light at the different wavelengths and capturing grey-scale images of the in vivo target illuminated at different wavelengths; and processing the captured grey-scale images to provide a multi-spectrum image of the in vivo imaging target. Herewith, the processing of the captured grey-scale images includes multispectral (or hyperspectral) processing, wherein image data (grey-scale) can be combined via an algorithm to yield a color or false-color image. In certain circumstances, the imaging can be true-color imaging (e.g., utilizing red, green, and blue light emissions) wherein the captured grey-scale images are recombined to provide a true-color image; or false-color imaging (e.g., utilizing infrared or ultraviolet light emissions, alone or with visible light emissions) wherein the captured grey-scale images are recombined and one or more of a non-visible emission is assigned to a visible band or visible bands are reassigned to accentuate differences in the imaging target.

While the compositions and methods of this invention have been described in terms of preferred embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A multi-spectrum ring illuminated surgical camera comprising:
    a ring lens that is configured as a unitary piece of fused silica or quartz and that includes a longitudinal axis, distal and proximal ends, an emission surface adjacent to the distal end, a reflector, an external surface, and a proximal void adjacent to the proximal end;
    a plurality of light emitting diodes (LEDs) carried within the proximal void, adjacent to an internal surface of the ring lens, and adapted to emit light radially with respect to the longitudinal axis, wherein the plurality of LEDs includes a first wavelength LED, a second wavelength LED, and a third wavelength LED; and
    a grey-scale image capture sensor adjacent to the emission surface and having imaging sensor electrical contacts electrically connected to an array contact post, which array contact post extends along said longitudinal axis through the ring lens.

2. The multi-spectrum ring illuminated surgical camera of claim 1, wherein the image capture sensor is recessed into the ring lens.

3. The multi-spectrum ring illuminated surgical camera of claim 1, wherein the image capture sensor includes an imaging array that is coplanar with the emission surface.

4. The multi-spectrum ring illuminated surgical camera of claim 1, further comprising a camera lens adjacent to the emission surface and adapted to focus light on the image capture sensor.

5. The multi-spectrum ring illuminated surgical camera of claim 1, wherein the plurality of LEDs includes a fourth wavelength LED.

6. The multi-spectrum ring illuminated surgical camera of claim 5, wherein the plurality of LEDs includes a fifth wavelength LED.

7. The multi-spectrum ring illuminated surgical camera of claim 1, wherein the plurality of LEDs includes at least two first wavelength LEDs.

8. The multi-spectrum ring illuminated surgical camera of claim 1, wherein the plurality of LEDs includes at least one white light LED.

9. The multi-spectrum ring illuminated surgical camera of claim 1, wherein the plurality of LEDs includes at least one LED that emits light in the UV or IR spectrum.

10. The multi-spectrum ring illuminated surgical camera of claim 1, wherein the ring lens is circular.

11. The multi-spectrum ring illuminated surgical camera of claim 1,
    wherein the reflector includes a reflection surface; and
    wherein at least one of the reflection surface and an external surface of the ring lens are mirrored.

12. The multi-spectrum ring illuminated surgical camera of claim 1, wherein the reflector is adapted to reflect the light along said longitudinal axis.

* * * * *